US011273444B2

United States Patent
Li et al.

(10) Patent No.: US 11,273,444 B2
(45) Date of Patent: Mar. 15, 2022

(54) INTEGRATED MICROFLUIDIC SYSTEM FOR DROPLET GENERATION, NUCLEIC ACID AMPLIFICATION, AND DETECTION

(71) Applicant: Precigenome, LLC, San Jose, CA (US)

(72) Inventors: Chen Li, Sunnyvale, CA (US); Yunfeng Ling, San Jose, CA (US); Cifeng Fang, Redmond, WA (US); Yaqi Wang, San Jose, CA (US); Yu Liu, San Jose, CA (US)

(73) Assignee: Precigenome, LLC, San Jose, CA (US)

( * ) Notice: Subject to any disclaimer, the term of this patent is extended or adjusted under 35 U.S.C. 154(b) by 0 days.

(21) Appl. No.: 17/285,450

(22) PCT Filed: Nov. 15, 2019

(86) PCT No.: PCT/US2019/061770
§ 371 (c)(1),
(2) Date: Apr. 14, 2021

(87) PCT Pub. No.: WO2020/102702
PCT Pub. Date: May 22, 2020

(65) Prior Publication Data
US 2021/0339248 A1 Nov. 4, 2021

Related U.S. Application Data

(60) Provisional application No. 62/768,715, filed on Nov. 16, 2018.

(51) Int. Cl.
*B01L 3/00* (2006.01)
*C12Q 1/68* (2018.01)
(Continued)

(52) U.S. Cl.
CPC ..... *B01L 3/502715* (2013.01); *B01L 3/50273* (2013.01); *B01L 3/502707* (2013.01);
(Continued)

(58) Field of Classification Search
CPC .......... B01L 3/502715; B01L 2200/10; B01L 3/502707; B01L 3/50273; B01L 7/52;
(Continued)

(56) References Cited

U.S. PATENT DOCUMENTS 9,910,012 B2   3/2018   Liu et al.
2005/0112634 A1   5/2005   Woudenberg et al.
(Continued)

FOREIGN PATENT DOCUMENTS

| CN | 104293945 A | 1/2015 |
| WO | 2010018465 A3 | 6/2010 |
| WO | 2017004250 A1 | 1/2017 |

OTHER PUBLICATIONS

PCT International Search Report and Written Opinion, International Application No. PCT/US2019/061770, International Filing Date, Nov. 15, 2019, 36 pages.

*Primary Examiner* — Brian J. Sines
(74) *Attorney, Agent, or Firm* — Umberg Zipser LLP; Jason Tejani (57) ABSTRACT

Disclosed herein are microfluidic devices and systems for amplifying and detecting a target polynucleotide, comprising: one or more wells for receiving one or more substrates; a droplet generation channel in fluid communication with the one or more wells, wherein the microfluidic channel is adapted to generate droplets; and a chamber in fluid communication with the droplet generation channel, and adapted to collect droplets generated by the droplet generation channel, and further adapted to perform nucleic acid amplification in droplets, and further adapted to detect light signal from droplets. Also disclosed are methods of using the same.

20 Claims, 11 Drawing Sheets

(51) Int. Cl.
    *C12M 1/00*           (2006.01)
    *C12P 19/34*         (2006.01)
    *C12Q 1/6806*       (2018.01)
    *C12Q 1/6844*       (2018.01)
    *C12Q 1/686*        (2018.01)
    *G01N 21/64*         (2006.01)

(52) U.S. Cl.
    CPC ....... *G01N 21/645* (2013.01); *G01N 21/6486*
        (2013.01); *B01L 2200/10* (2013.01); *B01L*
      *2200/12* (2013.01); *B01L 2200/142* (2013.01);
       *B01L 2300/0654* (2013.01); *B01L 2300/1805*
        (2013.01); *B01L 2400/0487* (2013.01); *C12Q*
       *1/6844* (2013.01); *G01N 2021/6471* (2013.01)

(58) Field of Classification Search
    CPC ..... B01L 3/00; G01N 21/6488; C12Q 1/6844;
           C12Q 1/68; C12Q 1/6806; C12Q 1/686;
                         C12M 1/00; C12P 19/34
    See application file for complete search history.

(56) References Cited

U.S. PATENT DOCUMENTS

| | | | |
|---|---|---|---|
| 2010/0173394 A1* | 7/2010 | Colston, Jr | B29C 45/006 |
| | | | 435/287.2 |
| 2015/0159224 A1 | 6/2015 | Zhang et al. | |
| 2019/0185909 A1* | 6/2019 | Li | B01L 3/5027 |
| 2019/0218594 A1 | 7/2019 | Abate et al. | |
| 2019/0345546 A1* | 11/2019 | Wang | C12Q 1/6825 |
| 2019/0352698 A1* | 11/2019 | Chang | B01L 3/50273 |

\* cited by examiner

INTEGRATED MICROFLUIDIC SYSTEM FOR DROPLET GENERATION, NUCLEIC ACID AMPLIFICATION, AND DETECTION

CROSS-REFERENCE TO RELATED APPLICATIONS

This application claims priority to U.S. Provisional Application No. with Ser. No. 62/768,715, filed on Nov. 16, 2018, the entire content of which is herein incorporated by reference.

FIELD OF THE INVENTION

The field of the invention relates to devices and methods for generating droplets, conducting nucleic acid amplification reactions in droplets and measuring reaction signal thereafter.

BACKGROUND

All publications herein are incorporated by reference to the same extent as if each individual publication or patent application was specifically and individually indicated to be incorporated by reference. Where a definition or use of a term in an incorporated reference is inconsistent or contrary to the definition of that term provided herein, the definition of that term provided herein applies and the definition of that term in the reference does not apply.

The following description includes information that may be useful in understanding the present invention. It is not an admission that any of the information provided herein is prior art or relevant to the presently claimed invention, or that any publication specifically or implicitly referenced is prior art.

Droplet Digital PCR (ddPCR) is a method based on water-in-oil emulsion technology. A sample is fractionated into tens of thousands of droplets, and PCR amplification of the template molecules occurs in each individual droplet if it contains template molecules. The benefit of ddPCR technology compared to the traditional real time PCR includes absolute quantification, unparalleled precision and increased sensitivity. A typical process includes droplet generation on a microfluidic chip, transfer of the droplets into PCR tubes (plate), PCR amplification in a thermal cycler instrument, and droplet fluorescence signal reading using a droplet reader instrument.

For example, in U.S. Pat. No. 9,631,230B2, Mark Davies et al disclosed a method of conducting a nucleic acid reaction, including methods for performing digital PCR using a "droplet-in-oil" technology. The droplets are passed in a continuous flow of immiscible carrier fluid through a channel that passes through a thermal cycler, whereby the target is amplified. However, this process includes several manual transfer steps, which is undesirable because it is labor intensive and there is a possibility for contamination.

WO2017004250A1 to Youngbull et al. discloses another system and method for continuous digital droplet PCR bioanalysis. However, this system does not have a built-in detection system. Thus, once the digital PCR system amplifies target DNAs in the droplets, the amplified target DNAs has to be manually transferred to be detected. This sort of manual transfer may cause undesirable post-PCR contaminations and is also labor intensive.

Thus, there is still a need for designing an integrated microfluidic system and device which can achieve the whole process without manual transfer of the sample by a user between the different steps.

SUMMARY OF THE INVENTION

The inventive subject matter provides an apparatus, systems and methods for an integrated microfluidic system and device that can achieve all the steps of digital PCR without several manual transfer steps, and without the undesirable post-PCR contamination.

In one aspect, the inventive subject matter provides a microfluidic device for amplifying and detecting a target polynucleotide, comprising: (a) one or more wells for receiving one or more substrates; (b) a droplet generation channel in fluid communication with the one or more wells, wherein the microfluidic channel is adapted to generate droplets; and (c) a chamber in fluid communication with the droplet generation channel, and adapted to collect droplets generated by the droplet generation channel, and further adapted to perform a chemical reaction in droplets, and further adapted to allow optical observation of the droplets. The chamber and the droplet generation channel are configured such that the hydrodynamic flow resistance of the chamber is smaller than the hydrodynamic flow resistance of droplet generation channel. The chamber depth is contemplated to be between 50% and 200% of the width or depth of the droplet generation channel such that the collected droplets inside the chamber are arranged in a monolayer fashion. The chamber volume is typically between 1 to 20 times of water phase volume used for droplet generation. The droplets formed may be a water-in-oil droplet, or an oil-in-water droplet. A number of chemical reactions are contemplated in the droplets; non-limiting examples include a polymerase chain reaction, a diagnostic reaction, or a restriction enzyme digestion.

In another aspect, the inventive subject matter provides a microfluidic system, comprising the microfluidic device as described herein, a thermal cycler comprising a flat surface adapted to receive the microfluidic device, and adapted to raise and lower the temperature of the surface in discrete, pre-programmed steps; and an optical detection unit comprising (a) one or more emission light generators, (b) an optical detector to detect reflected and/or fluoresced light, (c) a chip stage for receiving the microfluidic device, and (d) control and memory circuitry, wherein the control circuitry may move the chip stage in XYZ directions to scan the chamber area in the microfluidic device, and wherein the memory circuitry stores the intensity and wavelength of the reflected and/or fluoresced light detected by the optical detector.

The microfluidic system as disclosed herein may further comprise a pressure control device for generating droplets in the droplet generation channel. The microfluidic system may also further comprise a thermal cycling apparatus for conducting nucleic acid amplification in the chamber. In preferred embodiments, the microfluidic system may also comprise an optical reading control unit for optically detecting signal from the nucleic acid amplification inside droplets, counting number of droplets with higher and lower signal, and detecting the size of droplets. Furthermore, a software system is contemplated for calculating droplet percentage with lower and higher fluorescent signal, and size of droplets based on images taken from the optical unit.

The hydrodynamic resistance of the chamber is preferably 50 to 1000 times smaller than the hydrodynamic resistance of droplet generation channel, or more preferably 50 to 100 times smaller than the hydrodynamic resistance of droplet generation channel. The volume of the chamber is contemplated to be between 20 μL and 500 μL, and the depth of the chamber is between 20 μm to 500 μm, and more preferably between 40 μm to 200 μm. The width of the chamber is usually a few millimeters to a few centimeters, for example, 1 mm to 100 cm, or more preferably between 3 mm and 10 cm, or most preferably between 3 mm and 2 cm. The microfluidic channel is contemplated to connect chamber exit to the well. The device may comprise multiple droplet generation channels and/or multiple chambers, such as between 1 and 8 chambers, each of which is in fluid connection with each other and with a droplet generation channel.

Various embodiments of the present disclosure also include a method for droplet generation, nucleic acid amplification in droplets, and droplet signal detection in a single microfluidic device, providing a microfluidic device as disclosed herein, wherein the wells comprise a sample having a target nucleic acid to be amplified, and oil in a second well. The sample is then segmented to form sample encapsulated into water-in-oil droplets by providing a continuous flow of sample and oil through the droplet generation channel, and collecting the droplets in the chamber of the microfluidic device. The microfluidic device is placed on a thermal cycler that provides temperature cycles sufficient to perform nucleic acid amplification in the droplets, and is placed on an optics module for fluorescent detection and quantifying the amplified nucleic acid.

In preferred embodiments, the chamber and the droplet generation channel are configured such that the hydrodynamic flow resistance of the chamber is smaller than the hydrodynamic flow resistance of droplet generation channel. The chamber depth is between 50% and 200% of the width or depth of the droplet generation channel such that the collected droplets inside the chamber are arranged in a monolayer fashion. The chamber volume may be between 1 to 20 times of water phase volume used for droplet generation.

The fluorescent detection as disclosed herein may comprise orthogonal incident excitation light illumination or inclined incident excitation light illumination. The optics module may be further adapted to detect droplet size information. The droplet size information is detected by the steps comprising: (a) scanning the chamber of the microfluidic device to calculate the total number of droplets; and (b) using the droplet images to direct measure or calculate droplet size based on pixel information. The fluorescent signal intensity in each droplet may be used to calculate the percentage of droplets having positive fluorescence signal. The fluorescent signal intensity may also be used to calculate the averaged amount of amplified nucleic acids (e.g., DNA or RNA) in each droplet.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION

As described herein, in accordance with the various embodiments herein, the inventors have developed a microfluidic system and device with appropriate structures to conduct droplet generation, nucleic acid amplification (PCR), and fluorescence detection. The microfluidic device includes a substrate having channels and cross junction for droplet generation, a large chamber for hosting generated droplets and carrying nucleic acid amplification reaction, wells disposed on the substrate for reagent loading, and necessary channels for reagents flowing. The large chamber is positioned between two high resistance channels, where the flow resistances are at least 50 times higher than that of the chamber.

The microfluidic device as disclosed herein integrates droplet generation channels, PCR chamber for droplets, and fluorescence detection. As would be readily apparent to one of skill in the art, while the device and methods disclosed herein illustrate detection by fluorescence, other detection methods, for example, an enzymatic method, or chemiluminescent method may also be used for detection purposes.

In one aspect, the inventors have disclosed herein a microfluidic device, comprising one or more wells for receiving one or more substrates, a droplet generation channel in fluid communication with the one or more wells, wherein the microfluidic channel is adapted to generate droplets, and a chamber in fluid communication with the droplet generation channel, and adapted to collect droplets generated by the droplet generation channel, and further adapted to perform a chemical reaction in the droplets, and further adapted to detect light signal from droplets. The chamber and the droplet generation channel are configured such that the hydrodynamic flow resistance of the chamber is smaller than the hydrodynamic flow resistance of droplet generation channel. The chamber depth is between 50% and 200% of the width or depth of the droplet generation channel such that the collected droplets inside the chamber are arranged in a monolayer fashion. The chamber volume is between 1 to 20 times of water phase volume used for droplet generation.

The droplet may be a water-in oil droplet, or an oil-in-water droplet. A number of chemical reactions are contemplated to be performed in the droplet, for example a DNA amplification reaction, a restriction enzyme digestion, and/or a diagnostic reaction. The microfluidic device may further comprise a pressure control device for generating droplets in the droplet generation channel. The hydrodynamic resistance of the chamber is preferably 50 to 1000 times smaller than the hydrodynamic resistance of droplet generation channel, or more preferably 50 to 100 times smaller than the hydrodynamic resistance of droplet generation channel. The volume of the chamber is between 20 µL and 500 µL. The depth of the chamber is between 40 µm to 500 µm, or in some cases between 20 µm to 200 µm. The depths of channels are between 20 µm to 500 µm, and the width is usually a few centimeters. In some embodiments, a microfluidic channel is used to connect chamber exit to the well. In some embodiments, the device may comprise multiple droplet generation channels and/or multiple chambers, for example between 1 and 8 chambers, each of which are in fluid connection with each other and with a droplet generation channel.

In another aspect, the inventors have disclosed a microfluidic system, comprising the microfluidic device as described above, a thermal cycler comprising a flat surface adapted to receive the microfluidic device, and adapted to raise and lower the temperature of the surface in discrete, pre-programmed steps; and an optical detection unit comprising (a) one or more emission light generators, (b) an optical detector to detect reflected and/or fluoresced light, (c) a chip stage for receiving the microfluidic device, and (d) control and memory circuitry, wherein the control circuitry may move the chip stage in XYZ directions to scan the chamber area in the microfluidic device, and wherein the memory circuitry stores the intensity and wavelength of the reflected and/or fluoresced light detected by the optical detector. The system may further comprise a pressure control device for generating droplets in the droplet generation channel. The optical detection unit optically detects signal from the nucleic acid amplification inside droplets, counting number of droplets with higher and lower signal, and detecting the size of droplets. Furthermore, the microfluidic system may comprise a software system for calculating droplet percentage with lower and higher fluorescent signal, and size of droplets based on images taken from optical unit.

In another aspect, disclosed herein is a method for droplet generation, nucleic acid amplification in droplets, and droplet signal detection in a single microfluidic system, comprising providing a microfluidic system comprising (i) a microfluidic device having one or more wells for receiving one or more substrates; a droplet generation channel in fluid communication with the one or more wells, wherein the microfluidic channel is adapted to generate droplets; and a chamber in fluid communication with the droplet generation channel, and adapted to collect droplets generated by the droplet generation channel; (ii) a thermal cycler comprising a flat surface adapted to receive the microfluidic device, and adapted to raise and lower the temperature of the surface in discrete, pre-programmed steps; and (iii) an optical detection unit comprising one or more emission light generators, an optical detector to detect reflected and/or fluoresced light, a chip stage for receiving the microfluidic device, and control and memory circuitry, wherein the control circuitry may move the chip stage in XYZ directions to scan the chamber area in the microfluidic device, and wherein the memory circuitry stores the intensity and wavelength of the reflected and/or fluoresced light detected by the optical detector; providing a sample comprising a target nucleic acid in a first well, and oil in a second well; segmenting the sample to form sample encapsulated into oil droplets (e.g., oil-encapsulated sample droplets) by providing a continuous flow of sample and oil through the droplet generation channel, and collecting the oil-encapsulated sample droplets in the chamber of the microfluidic device; placing the microfluidic device on a thermal cycler which provides a temperature cycle sufficient to perform nucleic acid amplification in the droplets; and placing the microfluidic device on an optics module for fluorescent detection and quantification of the amplified nucleic acid in the oil encapsulated sample droplet. The chamber and the droplet generation channels are configured such that the hydrodynamic flow resistance of the chamber is smaller than the hydrodynamic flow resistance of droplet generation channel. The chamber depth is between 50% and 200% of the width or depth of the droplet generation channel such that the collected droplets inside the chamber are arranged in a monolayer fashion. The chamber volume is between 1 to 20 times of water phase volume used for droplet generation. The fluorescent detection may comprise orthogonal incident excitation light illumination or inclined incident excitation light illumination. The optics module may detect droplet size information, comprising the steps: scanning the chamber of the microfluidic device to detect the boundary of droplets and calculating the total number of droplets to form droplet boundary information; using the droplet boundary information to identify and locate the droplets; and using the droplet boundary information to find average droplet size, volume, and/or diameter of each of the droplets. The method disclosed herein may further comprise calculating fluorescent signal intensity of each droplet identified and located by the droplet boundary information, or calculating fluorescent signal intensity in each droplet to calculate the fluorescent signal intensity in each droplet, or calculating fluorescent signal intensity in each droplet to calculate the percentage of droplets having positive fluorescence signal, or calculating the concentration of the target polynucleotide by using the estimated average droplets volume based on the boundary information.

Figure 1:
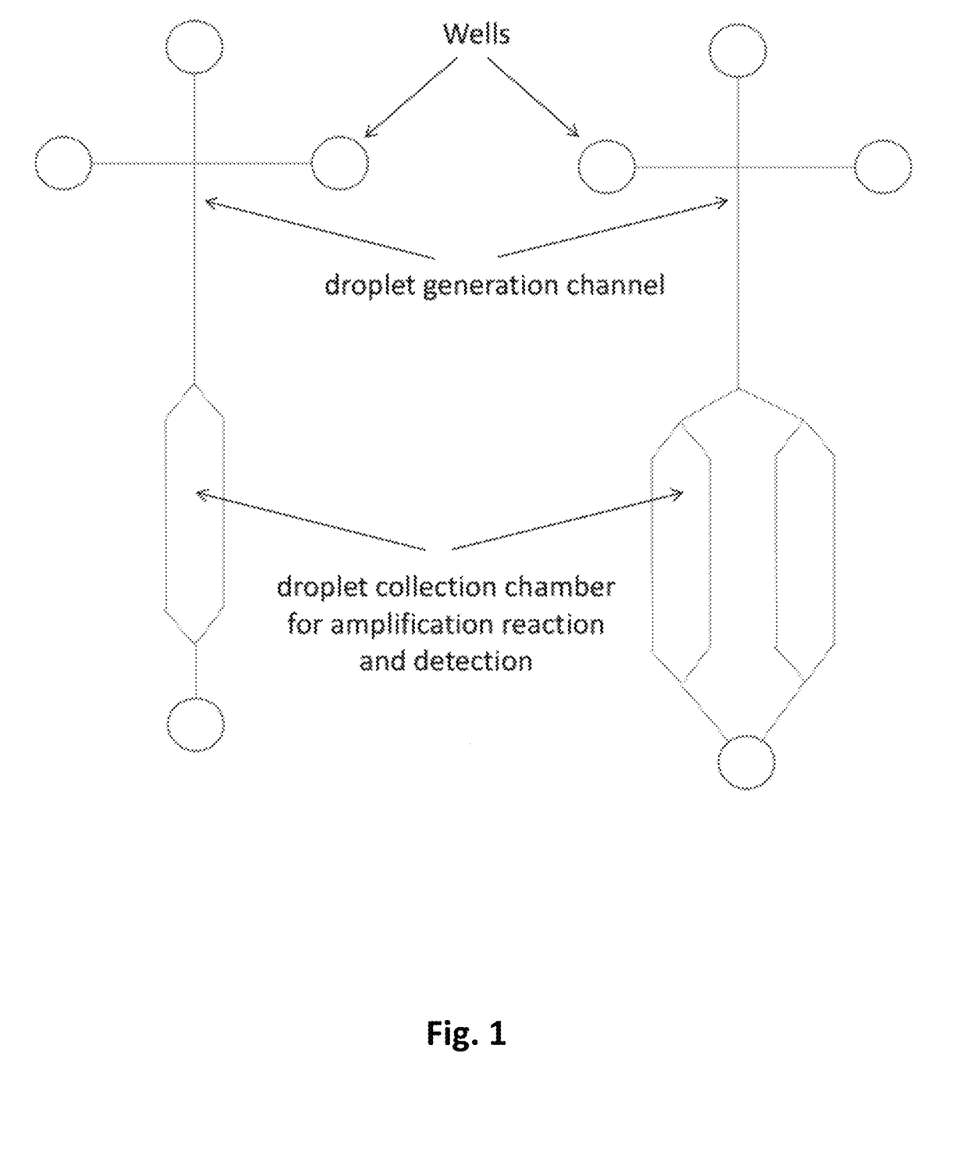
FIG. 1 depicts, in accordance with embodiments herein, schematic of an integrated microfluidic device. Left: one chamber design. Right: two chambers design. The number of the chambers is not limited, and there may be up to 8 different chambers.

FIG. 1 is a schematic of an integrated microfluidic device having droplet generation channels, a droplet collection chamber for PCR amplification and fluorescence detection, and wells for reagents loading. In order to generate droplet with diameter in a range of 30 µm-150 µm, the droplet generation channel dimension is in a range of 20 µm-150 µm (width and depth). A chamber is directly connected with droplet generation channel. For some cases, 2 or more chambers can be designed in order to compact the design and hold enough volume of droplets as shown in the right side of FIG. 1. These chambers are in fluid communication with the droplet generation channels. To avoid fluorescence interference among droplets, droplets should be packed inside the chamber in a monolayer fashion. To achieve this monolayer packing, the chamber depth design is based on the droplet size. The depth is in a range of 70%-130% of droplet diameter. Wells are used to hold reagents, for example oil and sample. The chamber volume is the total volume of oil and sample used during droplet generation process.

Figure 2:
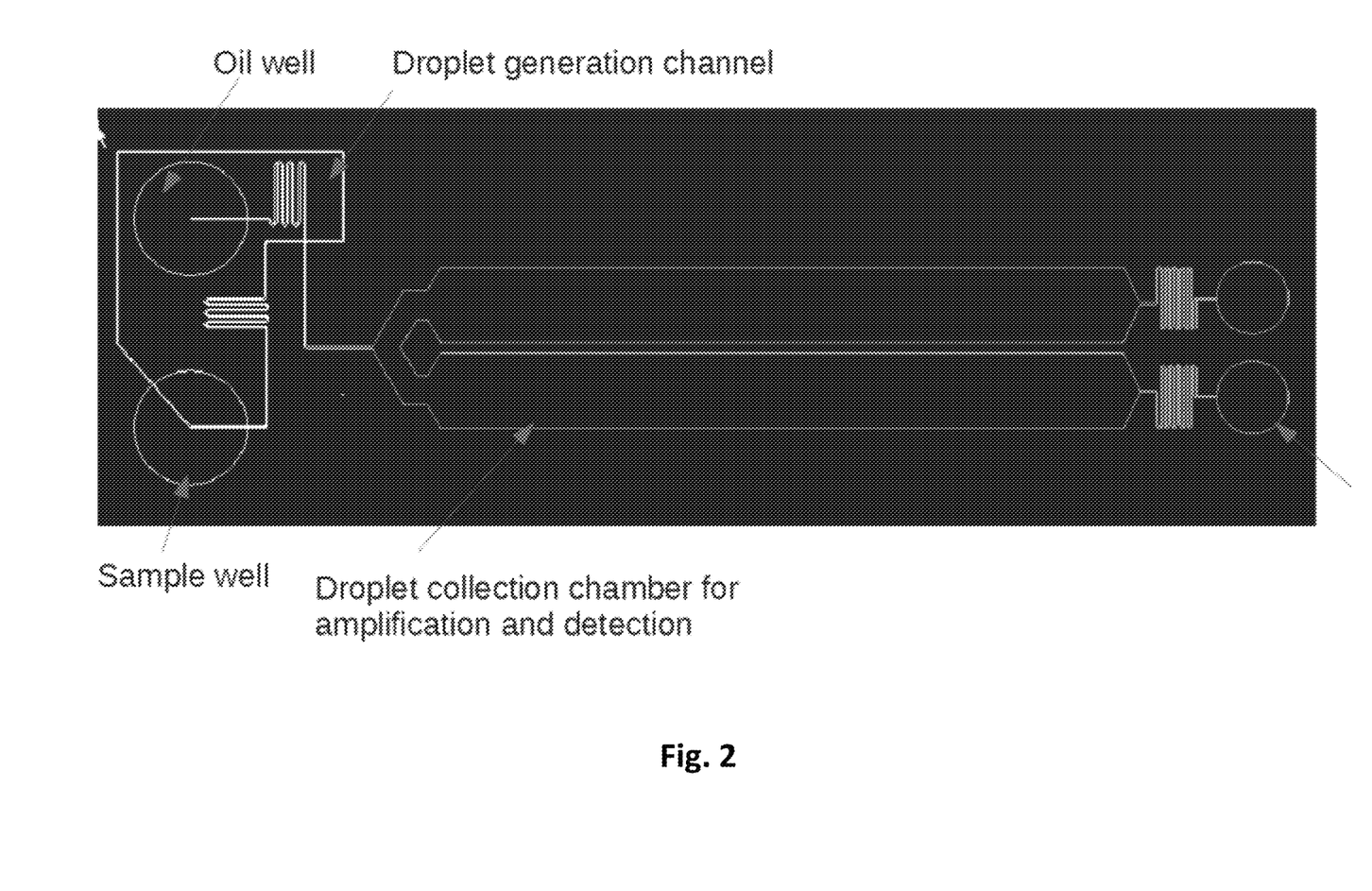
FIG. 2 depicts, in accordance with embodiments herein, an integrated microfluidic device design

FIG. 2 illustrates another design of the microfluidic device disclosed herein. In this embodiment, the depth of droplet generation channel is 85 μm. The width is the channel ranges from 70 μm to 90 μm depending on locations. By applying 2-3 psi pressure on oil and sample well, droplets with 110 μm in diameter can be generated. The depth of chamber is 120 μm, in which 110 μm size droplets can form monolayer. The total chamber volume is 40 μL. When 20 μL of sample is used for droplet generation, 20 μL of oil is consumed. In one embodiment, the channels are designed and the pressure applied to oil and sample phase is set in such a way that the oil to sample consumption ratio is 1:1.

Figure 4:
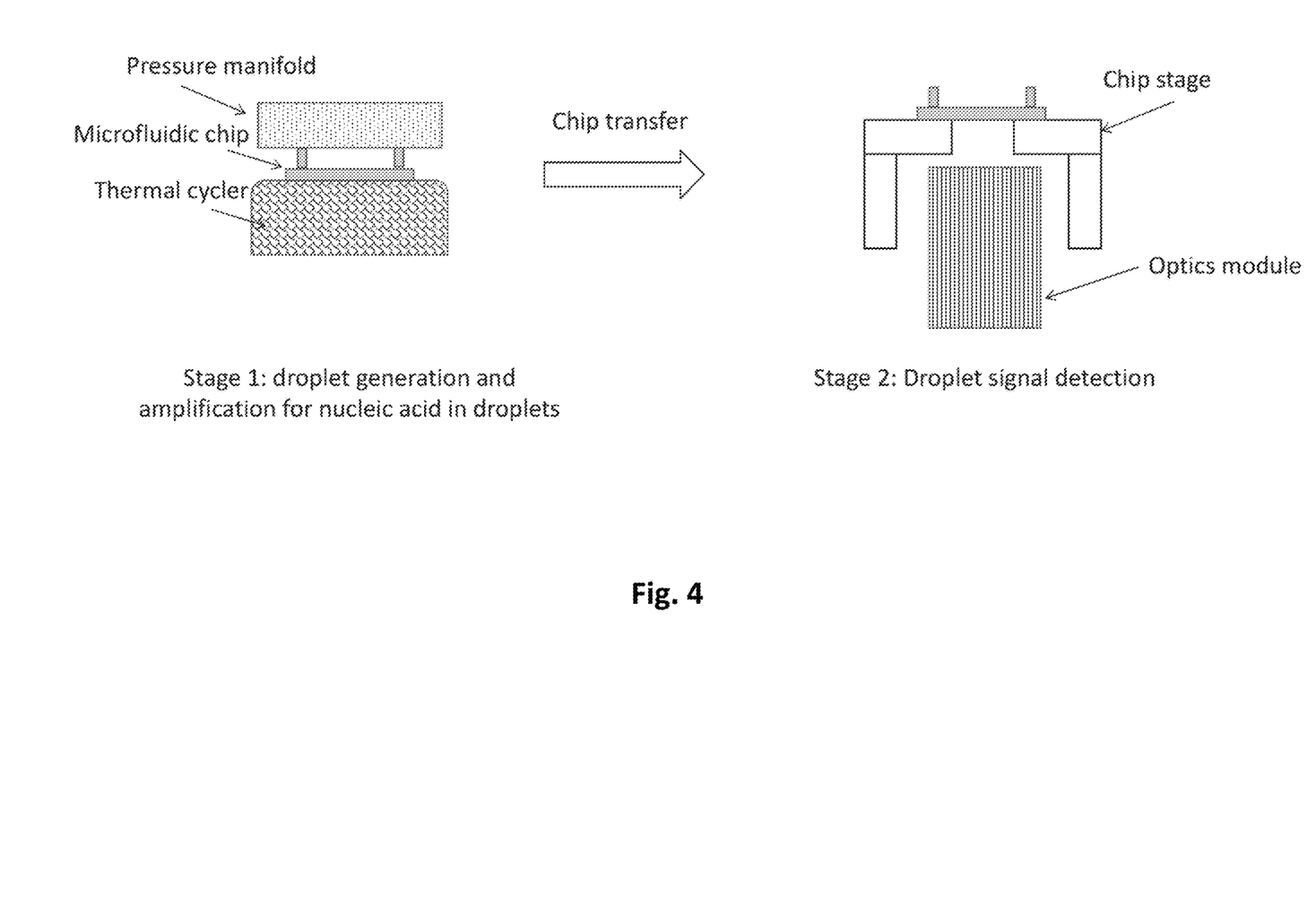
FIG. 4 depicts, in accordance with embodiments herein, schematic of microfluidic system for droplet generation, PCR amplification, and droplet fluorescence detection

Viewed from a different perspective, the inventors have disclosed a system which is used to achieve droplet generation, droplet collection in chamber, PCR reaction in chamber, and fluorescence detection as shown in FIG. 4. On Stage 1, a microfluidic device described above sits on top of a thermal cycler which provides temperature cycling. For example, a cycle of 95° C. for 30 seconds (s) and 55° C. for 1 minute inside the chamber for a total of 40 cycles can be achieved using the thermal cycler. A pressure manifold is used to form a good air tight seal. Pressure from 0-20 psi can be applied to wells on the microfluidic chip. To generate droplets in the microfluidic channel, different pressures are used to apply to oil well and sample well. For example, a pressure of 4.5 psi and 4.2 psi were applied to the sample well and oil well respectively to get 110 μm droplet size. After the droplets is collected and packed in the chamber, PCR reaction is started by applying temperature cycle on the film side of microfluidic chip using the thermal cycler. A pressure of 15 psi is applied through the manifold to all the wells on the microfluidic device to reduce evaporation and prevent bubble formation. After PCR reaction, the microfluidic chip is transferred to Stage 2 by mechanic transfer mechanism. On stage 2, the microfluidic chip sits on a chip stage. An optics module for bright field and fluorescence detection is under the chip stage. The chip stage can be moved in all directions, for example both horizontal and vertical direction. Viewed from another perspective, movement along X, Y, and Z axes are contemplated, such that the optics module can focus the light source inside chamber and scan the whole chamber area. The optics module can scan the droplet chamber to collect sizing information and fluorescent signal in multiple optical channels.

The optics module comprises of two main functional sub-modules. One sub-module is used to detect the fluorescent signal of droplets in the chamber. The other sub-module is used to detect the sizing information of the droplets. The optical detection system can be implemented by different approaches.

Figure 5:
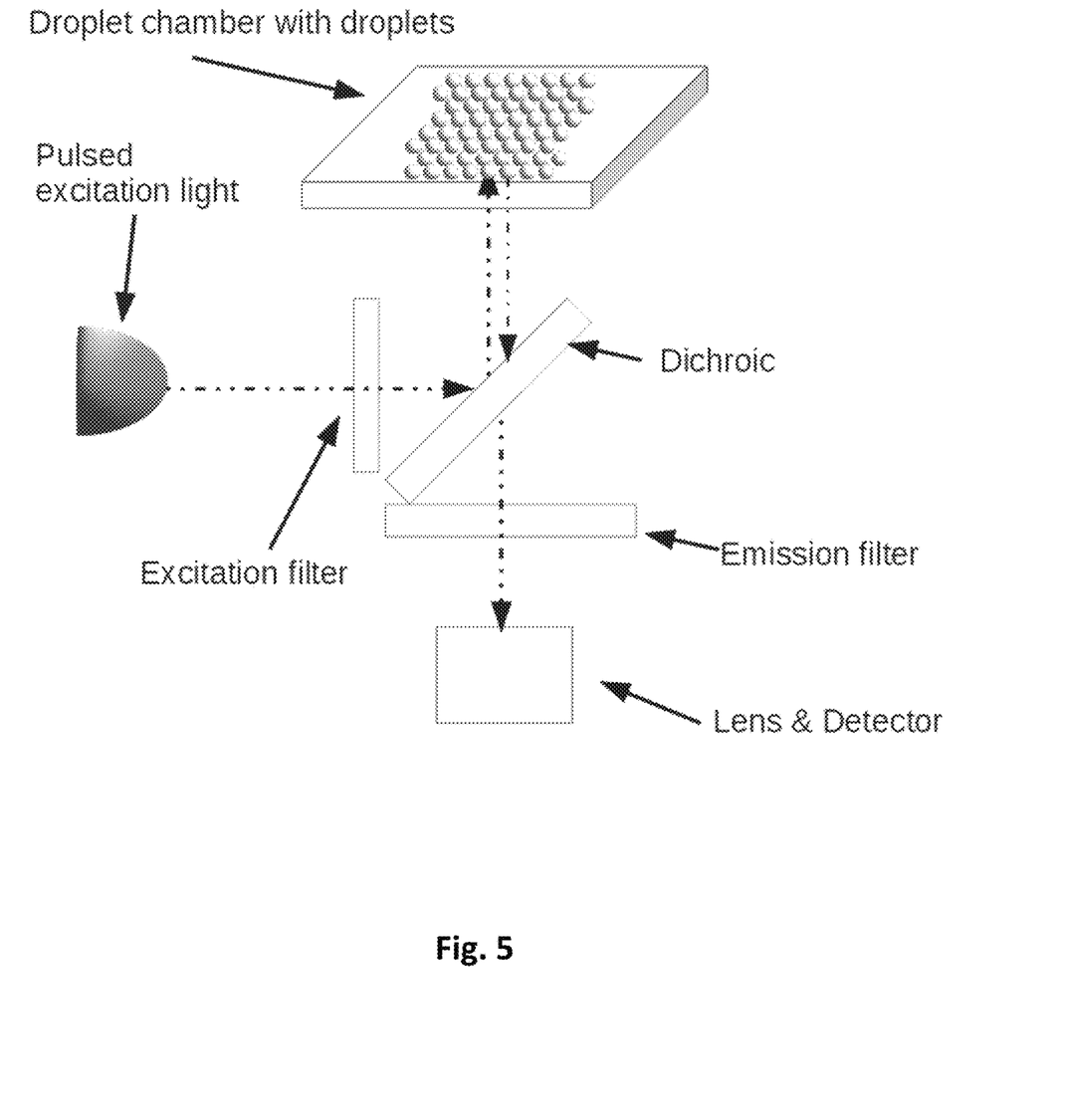
FIG. 5 depicts, in accordance with embodiments herein, a schematic view of fluorescent detection using orthogonal incident excitation light illumination

FIG. 5 illustrates fluorescent detection using orthogonal incident excitation light illumination. In order to be able to detect multiple fluorescent channels, excitation light, excitation filter, dichroic mirror and emission filter are assembled in to one mechanical structure for one specific fluorescent channel. Multiple assemblies can be installed together in the system, and each time one assembly is switched by a motion control system for that particular fluorescent channel detection. The excitation light is turned on by a pulsed controlled signal. Simultaneously, the fluorescent signal filtered by the emission filter is collected by the detector. The droplet data can be collected area by area using 2D image scanner or line by line by a line scanner, or the chip is moved by a XY motion stage for entire chamber scanning.

Figure 6:
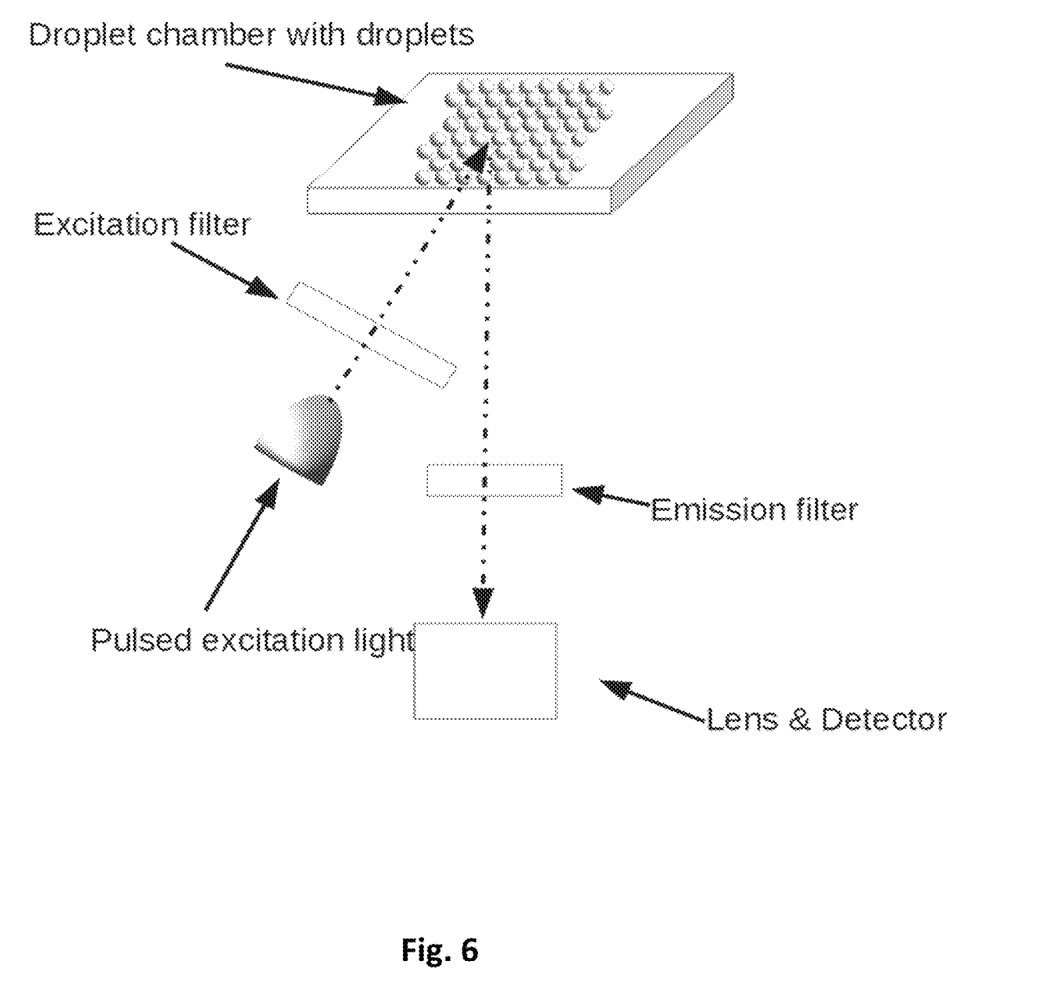
FIG. 6 depicts, in accordance with embodiments herein, a schematic view of fluorescent detection using inclined incident excitation light illumination

FIG. 6 shows the schematic of fluorescent detection using inclined incident excitation light illumination. In this implementation, the excited light is shined onto the droplet chamber with a inclined incident angle filtered by a excitation filter. It's also able to detect multiple fluorescent channel signal by switching the excitation light, excitation filter, dichroic mirror and emission filter for specific fluorescent channel, while the detector can be fixed.

Figure 7:
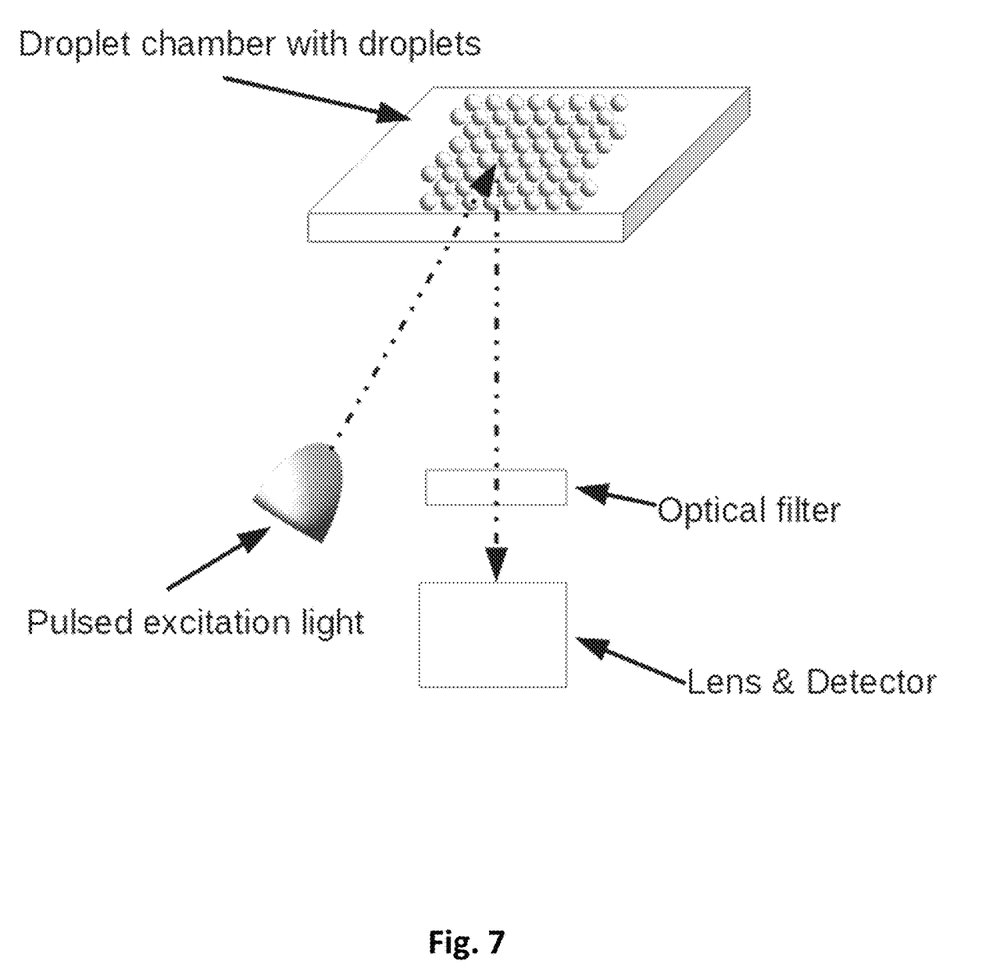
FIG. 7 depicts, in accordance with embodiments herein, a schematic view of droplet sizing information detection using inclined incident light illumination
Figure 8:
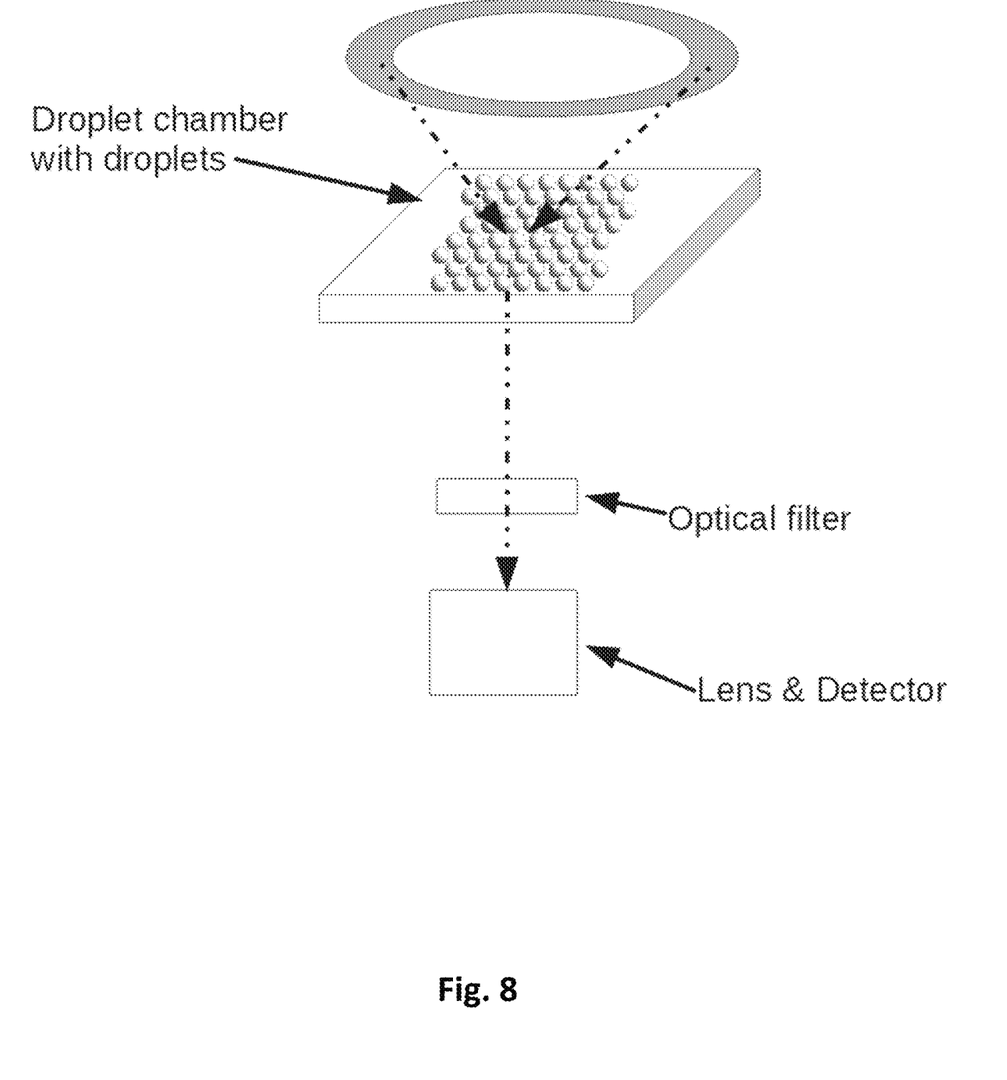
FIG. 8 depicts, in accordance with embodiments herein, a schematic view of droplet sizing information detection using ring light illumination

Sizing information is used to identify and locate the droplets in the chamber. It is collected by the optical sub-module by dark field or bright field illumination. FIG. 7 shows the schematic view of droplet sizing information detection using inclined incident light illumination. FIG. 8 shows the schematic view of droplet sizing information detection using ring light illumination.

Figure 9A:
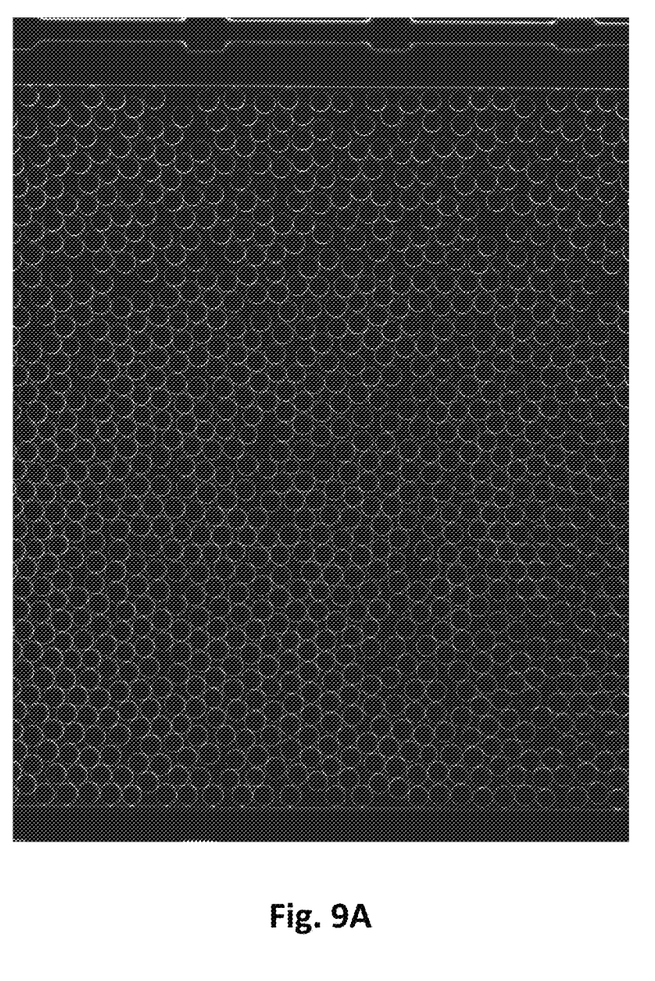
FIG. 9A depicts, in accordance with embodiments herein, a dark field image of a droplet sizing inside a chamber.
Figure 9B:
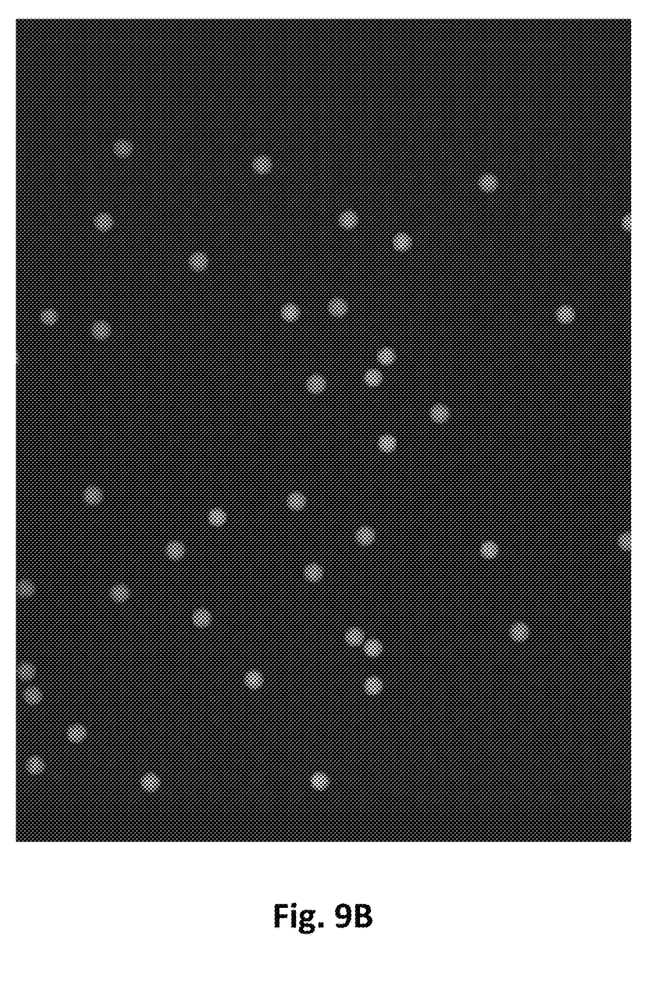
FIG. 9B depicts, in accordance with embodiments herein, a fluorescence image of a droplet sizing inside a chamber—(excitation: 495 nm emission: 520 nm).
Figure 10:
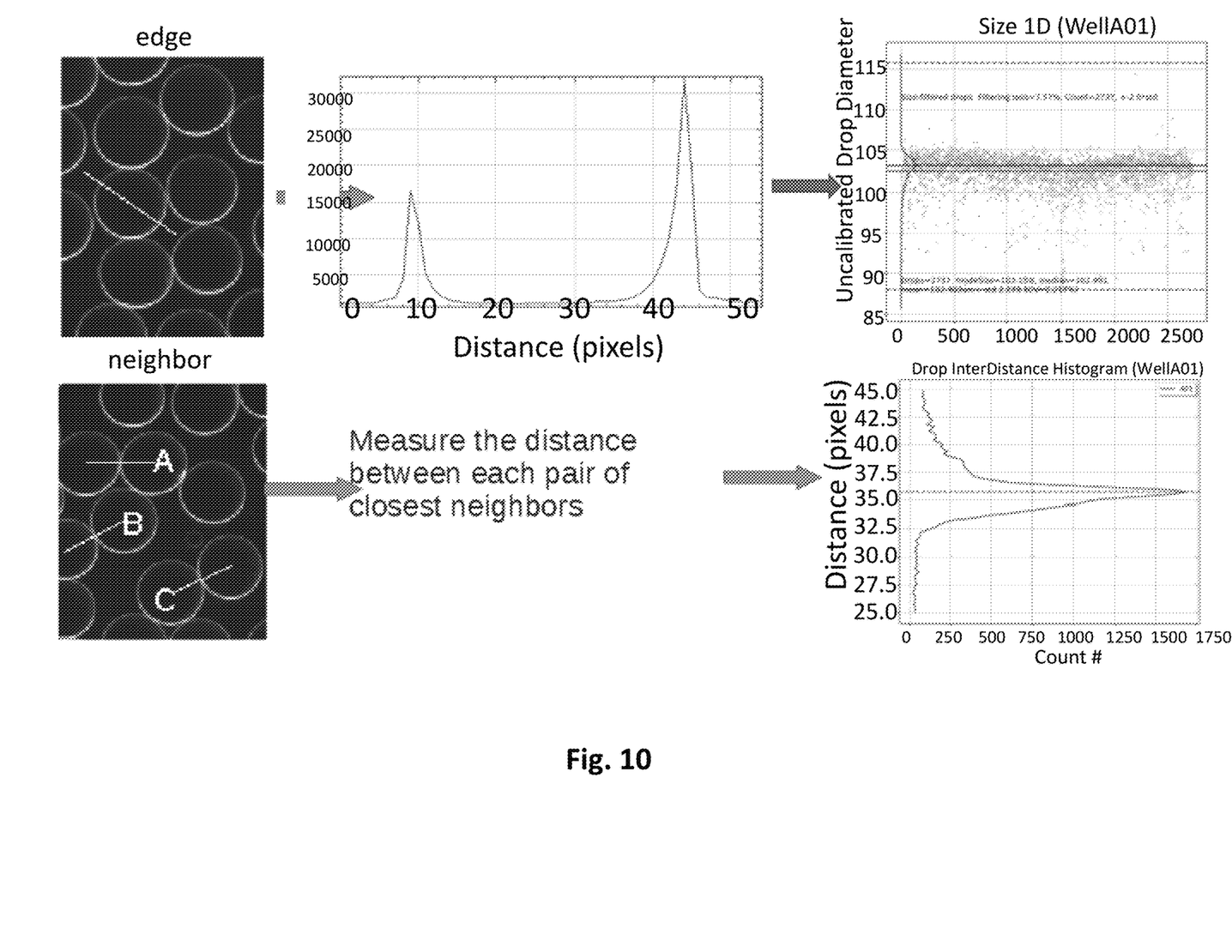
FIG. 10 depicts, in accordance with embodiments herein, an illustration of an exemplary calculation of droplet diameter based on dark field images using two different algorithms (edge detection method and nearest neighbor method) developed to calculate droplet diameter.

FIGS. 9A-9B show an example of data collected on Stage 2 after the PCR reaction. FIG. 9A shows a dark field image and FIG. 9B shows a fluorescence image (excitation: 495 nm emission: 520 nm). Based on the dark field images, algorithms are developed to calculate droplet diameter as shown in FIG. 10. Two algorithms are used to calculate the droplet diameter: edge detection method and smallest neighbor method. Using the edge detection method, the edge of the droplet was defined by the intensity difference. Two peaks for each droplet could be detected. The distance between the two peaks was used to calculate the droplet diameter. Using the nearest neighbor method, since most droplets are closely packed, the nearest droplet to droplet distance for the majority of the droplets is contemplated to be the diameter of droplets. Based on FIG. 9B (fluorescence data), the number of droplets having a positive fluorescence signal and the number and/or percentage of droplets with negative signal may be calculated. Finally, the formula below was used to calculate original DNA copy concentration.

$$c = \frac{-\ln(P_{negtive})}{\frac{1}{6}\pi D^3}$$

where c is DNA copy concentration (copy/uL); Pnegative is the percentage of negative signal percentage; D is the average diameter of droplets.

Figure 11:
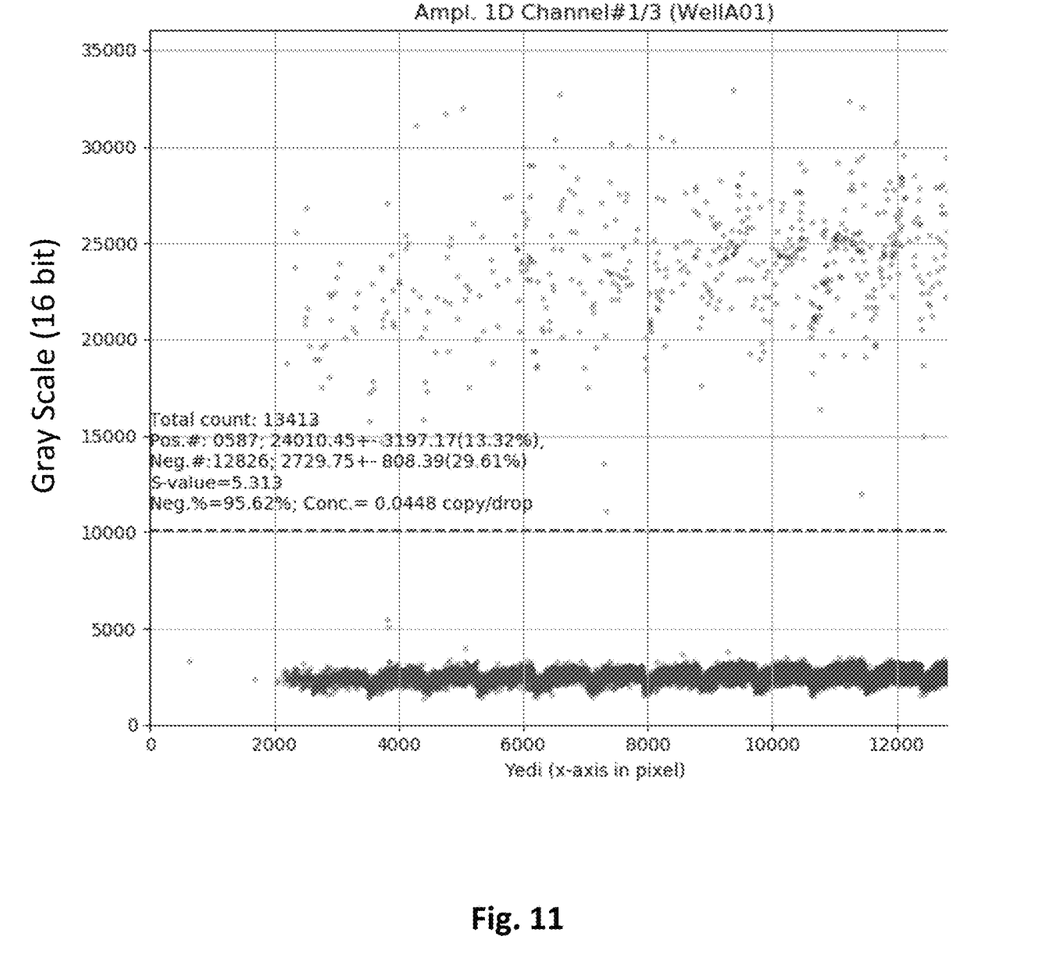
FIG. 11 illustrates an exemplary clustering of the droplet into two groups: positive and negative and calculation of the negative droplet percentage, indicated as 95.62% with a calculated concentration of 0.0448 copies/drop, as indicated.

FIG. 11 illustrates cluster of the droplet into two groups: positive and negative and calculated the negative droplet percentage (95.62%). The calculated concentration is 0.0448 copies/drop.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Embodiments of the present disclosure are further described in the following examples. The examples are merely illustrative and do not in any way limit the scope of the invention as claimed.

EXAMPLES

Example 1

PCR Process Using the Device Disclosed Herein

Figure 3A:
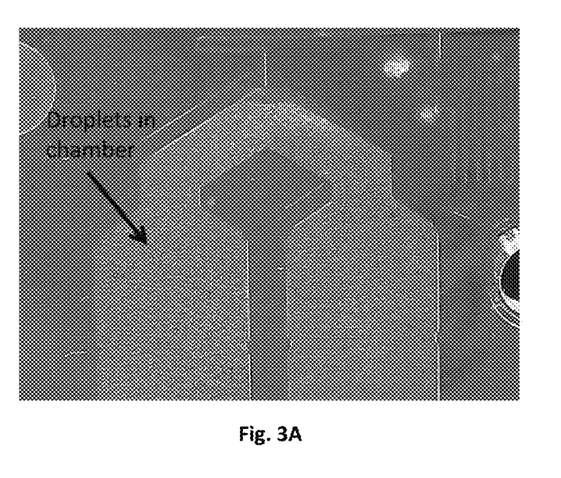
FIG. 3A depicts, in accordance with embodiments herein, droplets entering a chamber of an integrated microfluidic device as presently disclosed.
Figure 3B:
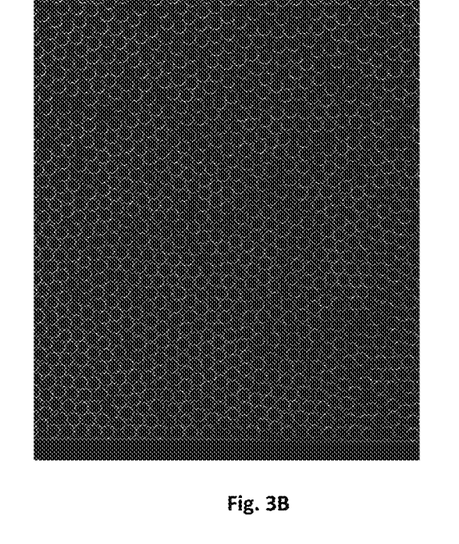
FIG. 3B depicts, in accordance with embodiments herein, a monolayer of droplets in a chamber of an integrated microfluidic device as presently disclosed.

In one embodiment, a typical process using the disclosed microfluidic device was described herein. 20 uL of sample is loaded in the sample well, and 90 uL of oil was loaded in the oil well of the microfluidic device. The chip was loaded in the system. The manifold was lowered, and different pressures (sample: 2.5 psi, oil: 2.2 psi) are applied to different wells to generate droplets. It typically takes 90 s. While generating droplets, the droplets enter the chamber (FIG. 3A) and were packed inside the chamber in a mono layer fashion (FIG. 3B).

After the droplet generation is done, 15 psi pressure was applied to all wells and the temperature cycle was started. An exemplary temperature cycle for PCR amplification is shown below:

98 C for 10 min
95 C for 30 s
55 C for 1 min} 40 cycles
Room temperature and hold After PCR amplification was completed, the microfluidic chip was transferred to the second stage. Bright field and fluorescence images were taken by the system. Data analysis was performed by software to give DNA concentration. As would be readily apparent to one of skill in the art, other temperatures, pressure, and times may be used as well to practice the method disclosed herein.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A microfluidic device, comprising:
one or more wells for receiving one or more substrates;
a droplet generation channel in fluid communication with the one or more wells, wherein the droplet generation channel is adapted to generate droplets; and
a chamber in fluid communication with the droplet generation channel, thereby rendering the chamber adapted to: (i) collect droplets generated by the droplet generation channel, (ii) perform a chemical reaction in the droplets, and (iii) detect a light signal from droplets,
wherein the chamber and the droplet generation channel are configured such that the hydrodynamic flow resistance of the chamber is smaller than the hydrodynamic flow resistance of droplet generation channel,
wherein the chamber depth is between 50% and 200% of the width or depth of the droplet generation channel such that the collected droplets inside the chamber are arranged in a monolayer fashion, and wherein the chamber volume is between 1 to 20 times of water phase volume used for droplet generation.

2. The microfluidic device of claim 1, wherein the droplet is a water-in oil droplet or an oil-in-water droplet.

3. The microfluidic device of claim 1, further comprising a pressure control device for generating droplets in the droplet generation channel and/or a thermal cycling apparatus for conducting nucleic acid amplification in the chamber.

4. The microfluidic device of claim 1, wherein the hydrodynamic resistance of the chamber is 50 to 1000 times smaller than the hydrodynamic resistance of the droplet generation channel.

5. The microfluidic device of claim 1,
wherein the chamber comprises:
a volume of between 20 µL and 500 µL; and/or
a depth of between 40 µm to 200 µm; and/or
wherein the droplet generation channel independently comprises a depth and a width of between 20 µm to 500 µm.

6. The microfluidic device of claim 1, further comprising a chamber exit and a microfluidic channel, wherein the microfluidic channel is used to connect the chamber exit to the one or more wells.

7. The microfluidic device of claim 1, wherein the device comprises between 1 and 8 chambers, each of which are in fluid connection with each other and with the droplet generation channel.

8. The microfluidic device of claim 1, wherein the chemical reaction is a nucleic acid amplification reaction and/or a diagnostic reaction.

9. A microfluidic system, comprising:
a microfluidic device according to claim 1;
a thermal cycling apparatus for conducting nucleic acid amplification in the chamber of the microfluidic device, the thermal cycling apparatus comprising a flat surface adapted to receive the microfluidic device, and adapted to raise and lower the temperature of the surface in discrete, pre-programmed steps; and
an optical detection unit comprising (a) one or more emission light generators, (b) an optical detector to detect reflected and/or fluoresced light, (c) a chip stage for receiving the microfluidic device, and (d) control and memory circuitry, wherein the control circuitry may move the chip stage in XYZ directions to scan the chamber area in the microfluidic device, and wherein the memory circuitry stores the intensity and wavelength of the reflected and/or fluoresced light detected by the optical detector.

10. The microfluidic system of claim 9, further comprising a pressure control device for generating droplets in the droplet generation channel.

11. The microfluidic system of claim 9, further comprising an optical reading control unit for optically detecting the light signal from the nucleic acid amplification inside the droplets, counting number of droplets with higher and lower signal, and detecting the size of droplets; and/or further comprising a software system for calculating a droplet percentage with lower and higher fluorescent light signal, and calculating a size of droplets based on images taken from the optical detection unit.

12. The microfluidic system of claim 9, wherein the hydrodynamic resistance of the chamber is 50 to 1000 times smaller than the hydrodynamic resistance of the droplet generation channel.

13. The microfluidic system of claim 9, wherein the chamber comprises:
a volume of between 20 µL and 500 µL; and/or
a depth of between 40 µm to 200 µm; and/or
wherein the droplet generation channel independently comprises a depth and a width of between 20 µm to 500 µm.

14. The microfluidic system of claim 9, further comprising a microfluidic channel and a chamber exit, wherein the microfluidic channel is used to connect the chamber exit to the one or more wells.

15. The microfluidic system of claim 9, wherein the device comprises between 1 and 8 chambers, each of which are in fluid connection with each other and with a droplet generation channel.

16. The microfluidic system of claim 9, wherein the system is for amplifying and detecting a target polynucleotide or for a diagnostic reaction.

17. A method for droplet generation, nucleic acid amplification in droplets, and droplet signal detection in a single microfluidic system, comprising:
a. providing a microfluidic system comprising:
   i. a microfluidic device having one or more wells for receiving one or more substrates; a droplet generation channel in fluid communication with the one or more wells, wherein the microfluidic channel is adapted to generate droplets; and a chamber in fluid communication with the droplet generation channel, wherein the chamber is adapted to collect droplets generated by the droplet generation channel;
   ii. a thermal cycler comprising a flat surface adapted to receive the microfluidic device, wherein the thermal cycler is adapted to raise and lower the temperature of the surface in discrete, pre-programmed steps; and
   iii. an optical detection unit comprising: (a) one or more emission light generators, (b) an optical detector to detect reflected and/or fluoresced light, (c) a chip stage for receiving the microfluidic device, and (d) control and memory circuitry, wherein the control circuitry may move the chip stage in XYZ directions to scan the chamber area in the microfluidic device, and wherein the memory circuitry stores the intensity and wavelength of the reflected and/or fluoresced light detected by the optical detector;
b. providing a sample comprising a target nucleic acid in a first well, and providing oil in a second well;
c. segmenting the sample to form oil-encapsulated sample droplets by providing a continuous flow of sample and oil through the droplet generation channel, and collecting the oil-encapsulated sample droplets in the chamber of the microfluidic device;
d. placing the microfluidic device on a thermal cycler which provides a temperature cycle sufficient to perform nucleic acid amplification in the oil-encapsulated sample droplets; and
e. placing the microfluidic device on an optics module for fluorescent detection and quantification of the amplified nucleic acid.

18. The method of claim 17, wherein the hydrodynamic flow resistance of the chamber is smaller than the hydrodynamic flow resistance of the droplet generation channel, and/or the chamber depth is between 50% and 200% of the width or the depth of the droplet generation channel such that the collected droplets inside the chamber are arranged in a monolayer fashion.

19. The method of claim 17, wherein the optics module further detects droplet size information, and wherein the droplet size information is detected by the steps comprising:
  a. scanning the chamber of the microfluidic device to detect at least one boundary of at least one droplet and calculating a total number of droplets to thereby produce droplet boundary information; and
  b. using the droplet boundary information to identify and locate the droplets; and
  c. using the droplet boundary information to find average droplet size, droplet volume, and/or droplet diameter.

20. The method of claim 19, further comprising calculating the concentration of the target polynucleotide by using an estimated average of droplet volume based on the droplet boundary information and a calculated percentage of droplets having positive and negative fluorescence signal.

\* \* \* \* \*